(12) United States Patent
Ouchi et al.

(10) Patent No.: US 6,685,723 B1
(45) Date of Patent: Feb. 3, 2004

(54) COMPONENT OF ENDOSCOPIC TREATMENT INSTRUMENT

(75) Inventors: Teruo Ouchi, Saitama (JP); Masaru Nagamine, Kagawa (JP)

(73) Assignee: Pentax Corporation, Tokyo (JP)

( * ) Notice: Subject to any disclaimer, the term of this patent is extended or adjusted under 35 U.S.C. 154(b) by 335 days.

(21) Appl. No.: 09/688,235

(22) Filed: Oct. 16, 2000

(30) Foreign Application Priority Data

Oct. 18, 1999 (JP) ............................................. 11-294683
Oct. 19, 1999 (JP) ............................................. 11-296086

(51) Int. Cl.$^7$ ............................................... A61B 17/28
(52) U.S. Cl. .................................................... 606/205
(58) Field of Search ................................ 606/205, 207, 606/208; 403/309

(56) References Cited

U.S. PATENT DOCUMENTS 6,013,095 A    1/2000    Ouchi

FOREIGN PATENT DOCUMENTS

| JP | 5-154095 | 6/1993 |
|----|----------|--------|
| JP | 7-111975 | 5/1995 |
| JP | 9-276285 | 10/1997 |

*Primary Examiner*—John J. Calvert
*Assistant Examiner*—James Smith
(74) *Attorney, Agent, or Firm*—Greenblum & Bernstein, P.L.C.

(57) ABSTRACT

A wire connecting link in an endoscopic treatment instrument has a mechanism connector formed at one end for establishing connection to a mechanism member, and a wire holder formed at the other end into which a manipulating wire is to be inserted and fixed. The wire connecting link is made from a single tubular workpiece which is flattened at one end to form the mechanism connector, and the remaining tubular part forms the wire holder.

6 Claims, 20 Drawing Sheets

FIG.25
FIG.26
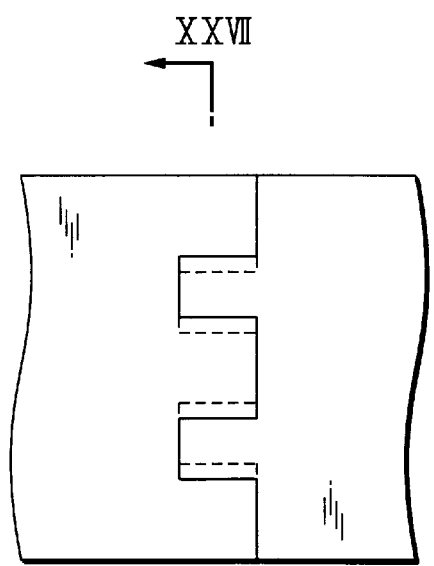
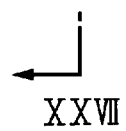

COMPONENT OF ENDOSCOPIC TREATMENT INSTRUMENT

BACKGROUND OF THE INVENTION

The present invention relates to an endoscopic treatment instrument, and in particular to a component of the endoscopic treatment instrument.

FIG. 32 shows the distal end portion of an endoscopic biopsy forceps which is one of the most commonly used endoscopic treatment instruments. A manipulating wire 2 is passed through a flexible sheath 1 to be capable of moving back and forth along the longitudinal axis. A distal end support member 3 is attached to the distal end of the sheath 1, and a pair of forceps cups 7 are supported on the member 3 such that they can open or close about a support shaft 5 like beaks.

A groove 3a open toward the front end is formed in the front portion of the distal end support member 3. A drive mechanism 10 that is actuated by the manipulating wire 2 to drive the forceps cups 7 to open and close is held within the groove 3a.

FIG. 33 shows the distal end support member 3 that is a component of the endoscopic treatment instrument. The rear portion 3A of the member 3 is formed like a tube into which the tip of the sheath 1 is to be inserted. The groove 3a into which the drive mechanism 10 is to be held is formed in the front portion 3B of the member 3.

To fabricate the distal end support member 3, a rod-shaped workpiece must be subjected to at least two cutting operations, one being drilling from the back and the other being the formation of a groove in the front portion. In addition, the use of a milling machine is required to increase the cost of component fabrication.

An object, therefore, of the invention is to provide a distal end support member for an endoscopic treatment instrument, which has a drive mechanism holding groove and a sheath connector and which can be manufactured at low-cost.

FIG. 14 shows a wire connecting link 90 which is connected to the distal end of the manipulating wire 2 as another component of the endoscopic treatment instrument. The link 90 has a mechanism connector 91 formed at one end and a wire holder 92 at the other end. The mechanism connector 91 has a hole 93 bored in a direction perpendicular to the longitudinal axis for establishing connection to the drive mechanism 10. The wire holder 92 has a hole 94 extending along the longitudinal axis into which the distal end of the manipulating wire 2 is inserted and fixed.

The manipulating wire 2 inserted into the hole 94 is silver brazed or otherwise fixed to the wire connecting link 90. Since brazing is effected at the mouth 94a of the hole 94, the wire holder 92 has a side hole 95 through which the operator can visually check if brazing material has flowed to the deepest part of the hole 94. The side hole 95 also functions to permit air to escape therethrough when the brazing material flows into the hole 94.

The provision of the side hole 95, however, has one serious problem. When a force is exerted on the wire connecting link 90 during service, the stress is concentrated around the side hole 95 to increase the chance of breaking of the link in areas near the side hole 95.

Another object, therefore, of the present invention is to provide a wire connecting link for an endoscopic treatment instrument, which makes it possible to positively check the state of the flow of a brazing material and which is durable because of the absence of any area where stress concentration occurs.

SUMMARY OF THE INVENTION

A wire connecting link according to a first aspect of the present invention includes a mechanism connector formed by flattening one end of a single tubular workpiece, and a wire holder formed by the rest of the tubular workpiece. This wire connecting link makes it possible to positively check the state of the flow of a brazing material during the brazing of a manipulating wire. This is realized without the provision of any area where stress concentration occurs, and therefore the wire connecting link is excellent in mechanical durability.

In an endoscopic treatment instrument of a preferred embodiment, a wire connecting link has a mechanism connector formed at one end for establishing connection to a mechanism member and a wire holder formed at the other end into which a manipulating wire is inserted and fixed. The wire connecting link is made from a single tubular workpiece which is flattened at one end to form the mechanism connector, the remaining tubular part forming the wire holder.

The tubular workpiece may be formed by bending or curving a sheet of workpiece into a tubular shape, with the resulting seam being left unclosed.

A distal end support member according to a second aspect of the invention includes a drive mechanism holding groove formed by bending a first strip of a metal blank in a U-shapem and a sheath connector formed by bending a second strip at right angles in a direction away from the first strip and then into an annular shape. The distal end support member does not require any cutting operations on a milling machine or the like, and can be fabricated mostly by press working. This contributes to a substantial reduction in the manufacturing cost and, hence, can realize the fabrication of disposable endoscopic treatment instruments that are effective in preventing inter-patient infection.

An endoscopic treatment instrument of a preferred embodiment has a distal end support member comprising a drive mechanism holding groove shaped in a U-form to hold a distal end treatment member drive mechanism in a movable fashion and a sheath connector shaped in an annular form to be capable of connection to the distal end of a sheath. A metal blank comprising a first strip and a second strip parallel thereto is deformed such that the first strip is bent in a U-shape to form the drive mechanism holding groove while the second strip is wholly bent at right angles in a direction away from the first strip and further bent in an annular shape to form the sheath connector.

The second strip may consist of two parts connecting to opposite sides of the first strip. If the first strip is formed to be thicker than the other parts of the blank, the resulting drive mechanism holding groove can have adequate mechanical strength.

The sheath connector may consist of two parts joined together in a single ring. The joining parts of the sheath connector may have interlocking portions that prevent them from slipping out of each other in a circumferential direction.

The end faces of the joining parts of the sheath connector may include a plurality of inclined surfaces that contact each other at an angle such that one joining part underlies the other joining part in a radial direction and that an area where one joining part underlies the other joining part alternates with an area where said one joining part overlies the other joining part.

The present disclosure relates to the subject matter contained in Japanese patent application Nos. Hei. 11-294683 (filed on Oct. 18, 1999) and Hei. 11-296086 (filed on Oct. 19, 1999), which are expressly incorporated herein by reference in their entireties.

BRIEF DESCRIPTION OF THE DRAWINGS

FIG. 25 is section XXV—XXV of FIG. 24;

FIG. 26 is a front view of yet a third modification of the joining parts of the distal end support member;

DESCRIPTION OF THE PREFERRED EMBODIMENT

Embodiments of the invention are described below with reference to accompanying drawings.

Figure 1:
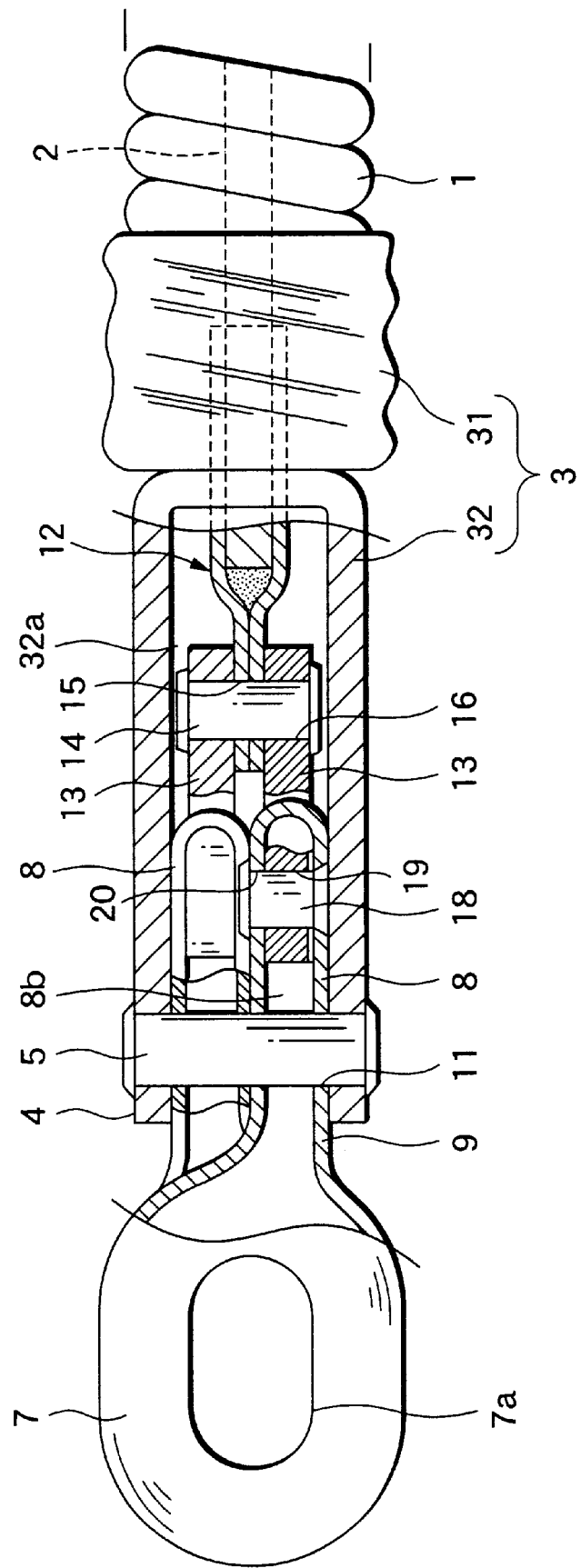
FIG. 1 is a plan view showing different sections of the distal end portion of an endoscopic biopsy forceps in a closed state according to a first embodiment of the invention.
Figure 2:
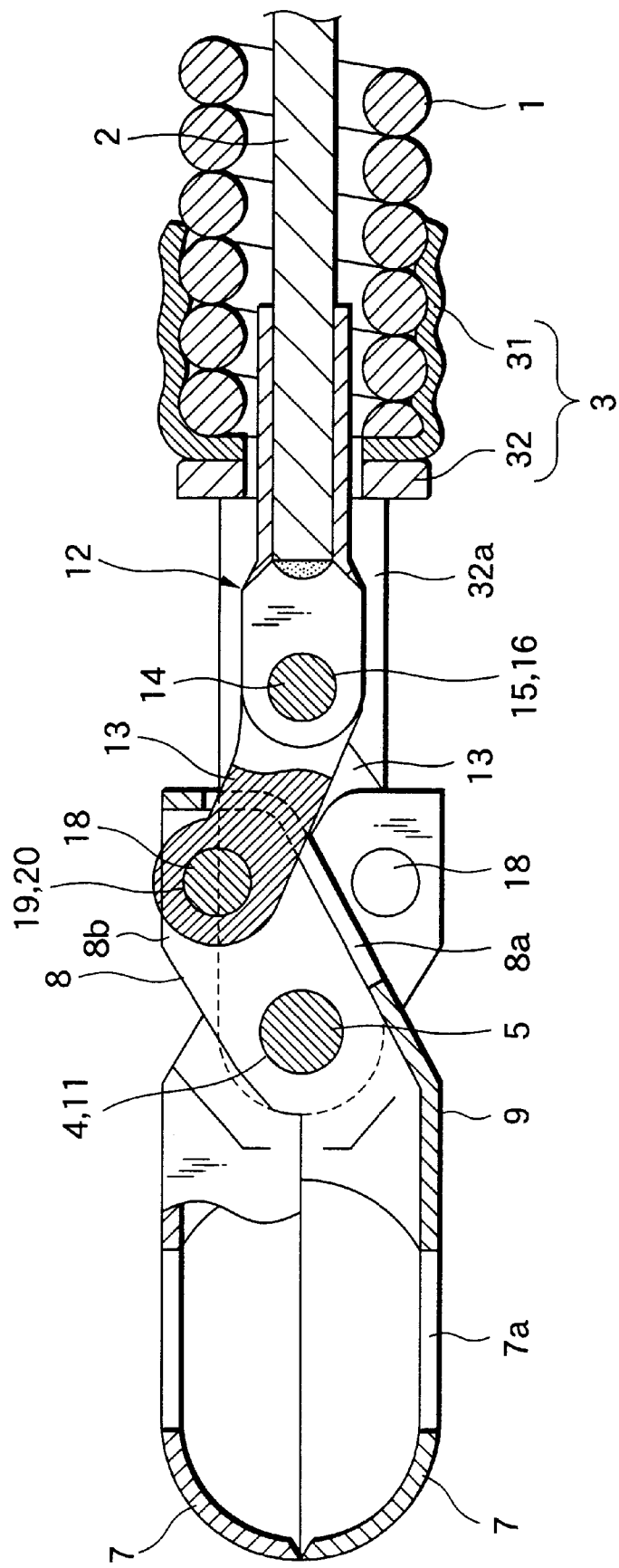
FIG. 2 is a side view showing different sections of the distal end portion of the endoscopic biopsy forceps in a closed state according to the first embodiment of the invention.

FIG. 1 is a plan view showing, partly in section, the distal end portion of an endoscopic biopsy forceps according to a first embodiment of the invention. FIG. 2 is a side view showing, partly in section, the same distal end portion. To save space, different sections are shown in one sheet in each of FIGS. 1 and 2.

A flexible sheath 1 to be passed into or removed from a forceps channel (not shown) in an endoscope is a tube in coil form made by winding a metal wire, typically a stainless steel wire, in close turns of a given diameter.

The sheath 1 may have other constructions; for example, the tube in coil form may be covered with a flexible tube to make the sheath 1. The sheath 1 has a length of about 1–2.5 m and a diameter of about 1.5–3 mm.

A manipulating wire 2 extends through the entire length of the sheath 1 in such a way that it can be moved back and forth along the longitudinal axis by manipulation from a manipulating section (not shown) connected to the basal end of the sheath 1.

A distal end support member 3 is securely connected to the distal end of the sheath 1. The distal end support member 3 includes an annular connector 31 for connection to the distal end of the sheath 1, and a support frame 32 in U shape that is fixed to the front of the annular connector 31.

In the embodiment under consideration, the annular connector 31 is a cap-shaped member having a spiral groove in the surface that can be threaded over the distal end of the sheath 1. The support frame 32 is formed by bending a sheet of workpiece into U shape and, with its open end facing forward, and the rear end portion is fixed to the annular connector 31. A hole through which a wire connecting link 12 (described later) is to be passed loosely is formed along the central axis of the area where the annular connector 31 is fixed to the support frame 32.

The distal end support member 3 has a support shaft receiving hole 4 bored through an area near its distal end (i.e., near the distal end of the support frame 32) in a direction perpendicular to the longitudinal axis, and a support shaft 5 is passed through the hole 4 and crimped at both ends.

Two sets of members, each of which is an integral assembly of a forceps cup 7 and a drive lever 8, are pivotally supported on the support shaft 5. A pair of forceps cups 7, with the open sides facing each other, are provided to project forward from the distal end support member 3.

Figure 3:
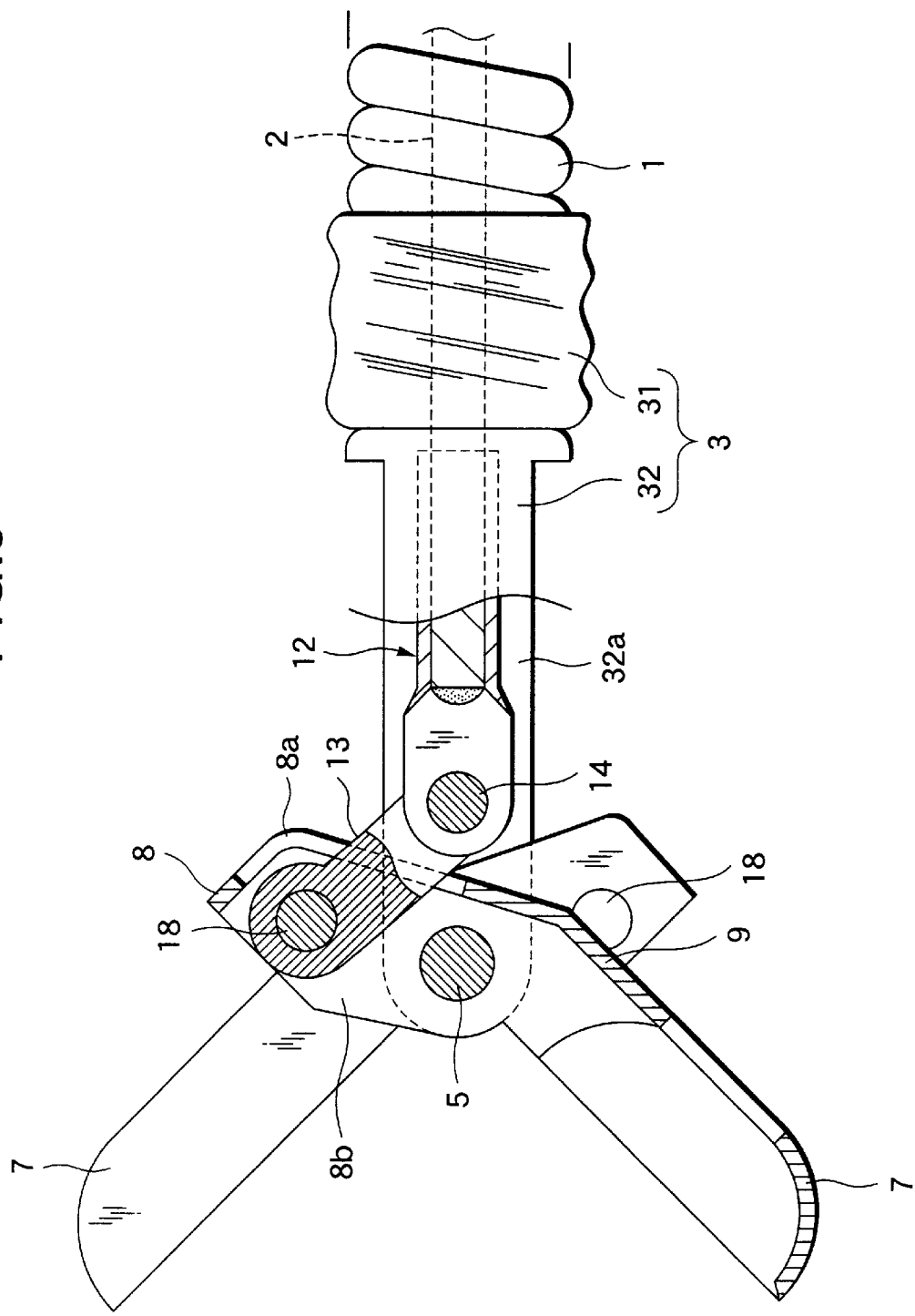
FIG. 3 is aside view showing different sections of the distal end portion of the endoscopic biopsy forceps in an open state according to the first embodiment of the invention.

The drive levers 8 are accommodated in a movable fashion in a groove 32a in the U-shaped support frame 32. The support shaft 5 held at both ends by the distal end support member 3 is passed through shaft holes 11 in the drive levers 8. When the drive levers 8 pivot about the support shaft 5, the forceps cups 7 integral with the drive levers 8 open and close like beaks. FIG. 3 shows the forceps cups 7 in the open state.

Figure 4:
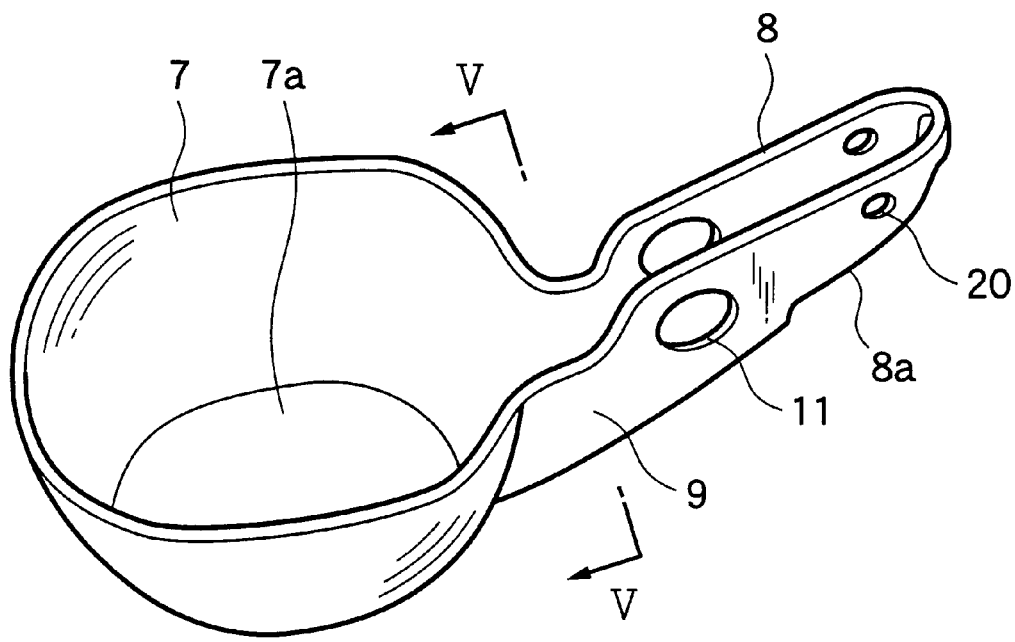
FIG. 4 is a perspective view of a member which is an integral combination of forceps cup and drive lever in the endoscopic biopsy forceps according to the first embodiment of the invention.

The forceps cups 7 and the drive levers 8 are formed from a single stainless steel sheet by pressing. FIG. 4 is a perspective view of forceps cup 7 and drive lever 8 in integral combination. A plan view of the combination is shown partly in section in FIG. 1.

The combination of forceps cup 7 and drive lever 8 is generally formed as a spoon with a short handle. The forceps cup 7 is a semi-oval member having an opening 7a in the back, with a blade formed along the edge of the open side.

Figure 5:
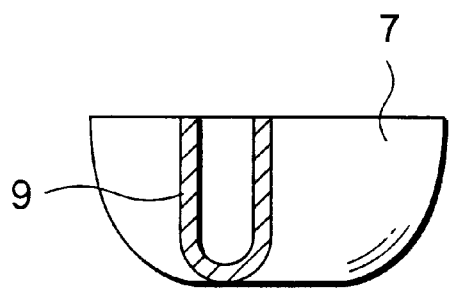
FIG. 5 is section V—V of FIG. 4 showing the boundary between the forceps cup and the drive lever in the endoscopic biopsy forceps according to the first embodiment of the invention.

The boundary 9 between the forceps cup 7 and the drive lever 8 has a generally U-shaped cross section as shown in FIG. 5 which is section V—V of FIG. 4. The drive lever 8 also has a generally U-shaped cross section continuous from the boundary 9. The continuous portion having a generally U-shaped cross section presents high strength since its bottom works as a beam that counteracts lateral forces.

The distal end portion of the wire connecting link 12 securely connected to the distal end of the manipulating wire 2 is positioned within the groove 32a in the distal end support member 3. Two link plates 13 placed on opposite sides of the distal end portion of the wire connecting link 12 are pivotally connected to the wire connecting link 12 in an area near its distal end by means of a rivet 14.

The rivet 14 is loosely and rotatably passed through a hole 15 in the wire connecting link 12 and its opposite ends are retained in holes 16 in the two link plates 13 and crimped.

The hollow spaces 8b in the generally U-shaped drive levers 8 provide parallel grooves formed in a direction perpendicular to the longitudinal axis of the support shaft 5. The other end of each link plate 13 is inserted into the associated groove 8b, and the link plates 13 are pivotally connected to the drive levers 8 by means of rivets 18 (pin-shaped members) each being retained by the associated drive lever 8 at both ends.

The two rivets 18 are rotatably and loosely fitted through holes 19 formed in the link plates 13, and each of them is retained at both ends by a hole 20 made in the associated drive lever 8. Shown by 8a is an opening made in the bottom of each drive lever 8 to allow for passage of the associated link plate 13.

Thus, the wire connecting link 12, the two link plates 13 and drive levers 8 constitute a link mechanism in the form of a pantograph. When the operator manipulates the wire 2 so that it is moved back and forth, the wire connecting link 12 is accordingly moved back and forth so that the drive levers 8 are allowed to pivot about the support shaft 5 by means of the link plates 13, causing the forceps cups 7 to open and close like beaks.

Figure 6:
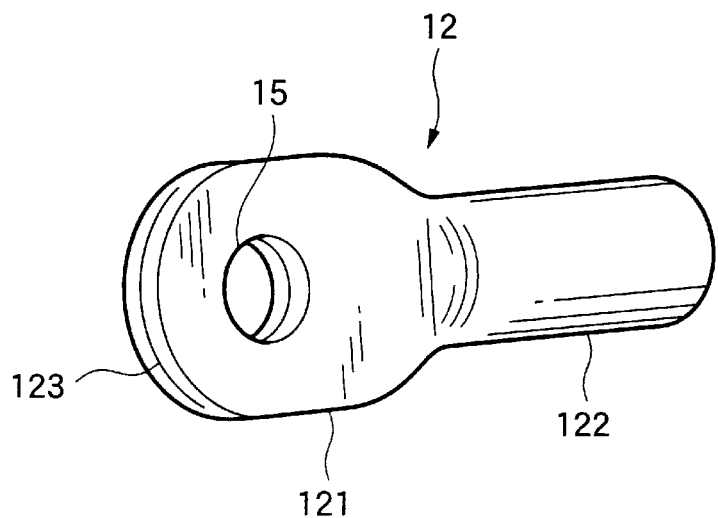
FIG. 6 is a perspective view of a wire connecting link according to the first embodiment of the invention.

The thus constructed wire connecting link 12 in endoscopic biopsy forceps is formed from a tubular workpiece, as shown in section in FIGS. 1, 2 and 3 and as is clear from FIG. 6 which shows the external appearance of the link.

Figure 7:
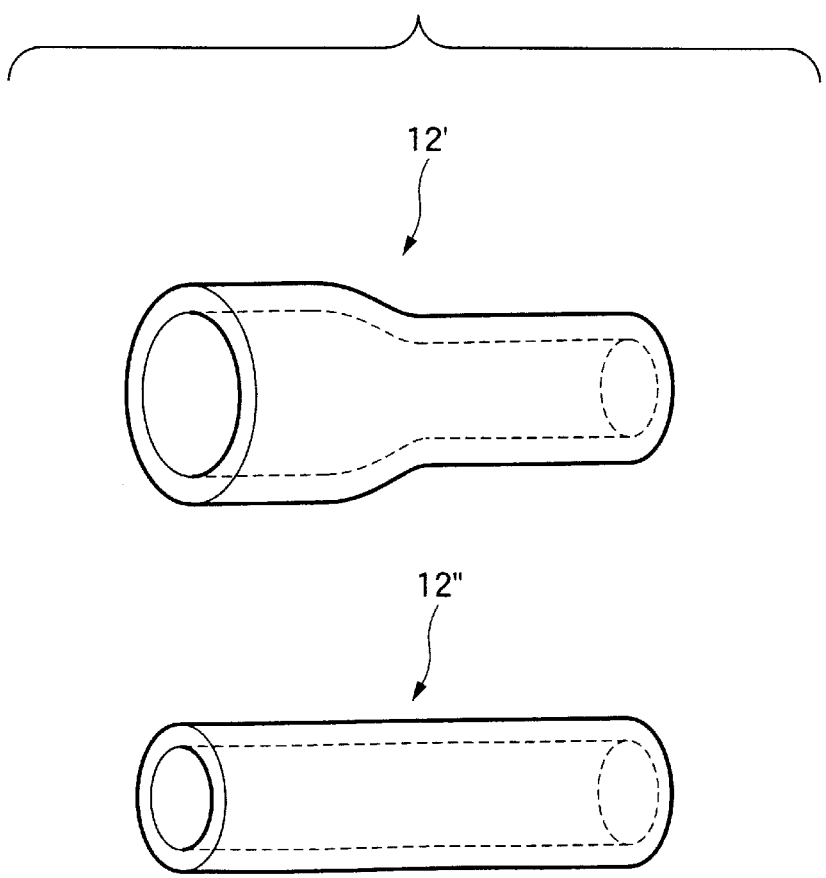
FIG. 7 is a perspective view of a tubular workpiece according to the first embodiment of the invention.
Figure 8:
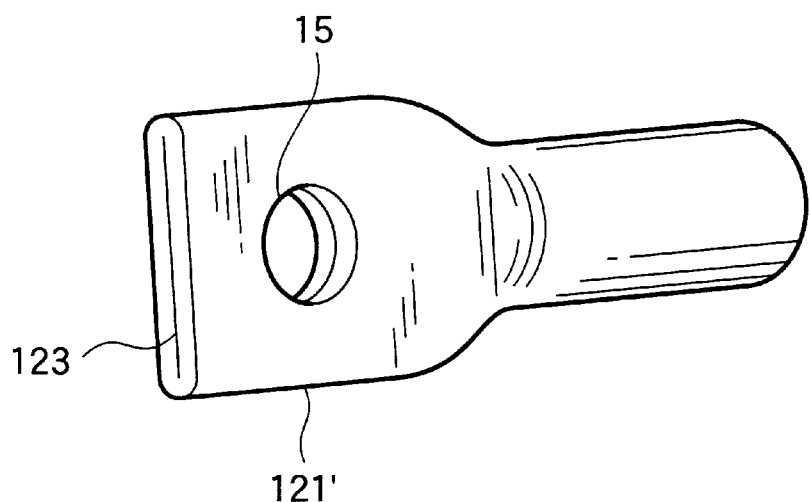
FIG. 8 is a perspective view of an unfinished wire connecting link according to the first embodiment of the invention.

FIG. 7 shows tubular workpieces 12' and 12" from which the wire connecting link 12 can also be fabricated. The workpiece 12' is a seamless stainless steel pipe having a larger diameter in the front part than in the rear part. The workpiece 12" is also a seamless stainless steel pipe but it has the same diameter throughout its length.

To fabricate the wire connecting link 12 from the tubular workpiece 12' (or 12"), its front part is pressed on both sides to form a flattened portion 121 (serving as a mechanism connector 121) in the center position through which the longitudinal axis passes. A hole 15 for establishing connection to the link plates 13 is made in the flattened portion 121. Indicated by 123 is a slot of very small gap formed between the inner surfaces of the flattened area.

The front corners of the flattened area are rounded off to form a wire connecting link generally indicated by 12 in FIG. 6. As shown in FIG. 6, the link 12 includes the flattened portion at one end which provides the mechanism connector 121 for establishing connection to the link plates 13, and the remaining tubular portion which provides a wire holder 122 for establishing connection to the manipulating wire 2. Almost all stages of the production of the wire connecting link 12 can be accomplished by pressing at low cost.

Figure 9:
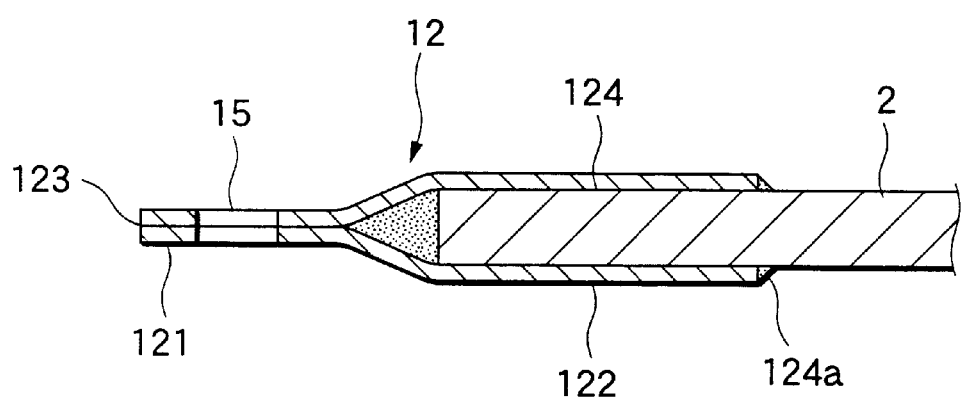
FIG. 9 is a plan view showing in section the step of securing a manipulating wire to the wire connecting link according to the first embodiment of the invention.

FIG. 9 shows the wire connecting link 12 into which the manipulating wire 2 has been inserted and secured. The manipulating wire 2 inserted into the bore 124 of the wire connector 122 is silver brazed or otherwise secured to the wire connecting link 12.

While the brazing operation is performed at the mouth 124a of the bore 124, the air in the bore 124 passes through the slit 123 to go outside. When the brazing material starts to flow out of the slit 123, the operator can say for sure that the bore 124 has been filled up with the brazing material.

The thus constructed wire connecting link 12 has no side hole or other cuts formed in the wire connector 122, and in the absence of any areas where the stress of an external force will concentrate, the link 12 is not easy to break.

The present invention is by no means limited to the foregoing embodiment. According to a second embodiment shown in FIG. 10, a sheet of workpiece is curved in a tubular form and the resulting seam 120 is left unclosed, forming a tubing 12' (or 12").

Figure 10:
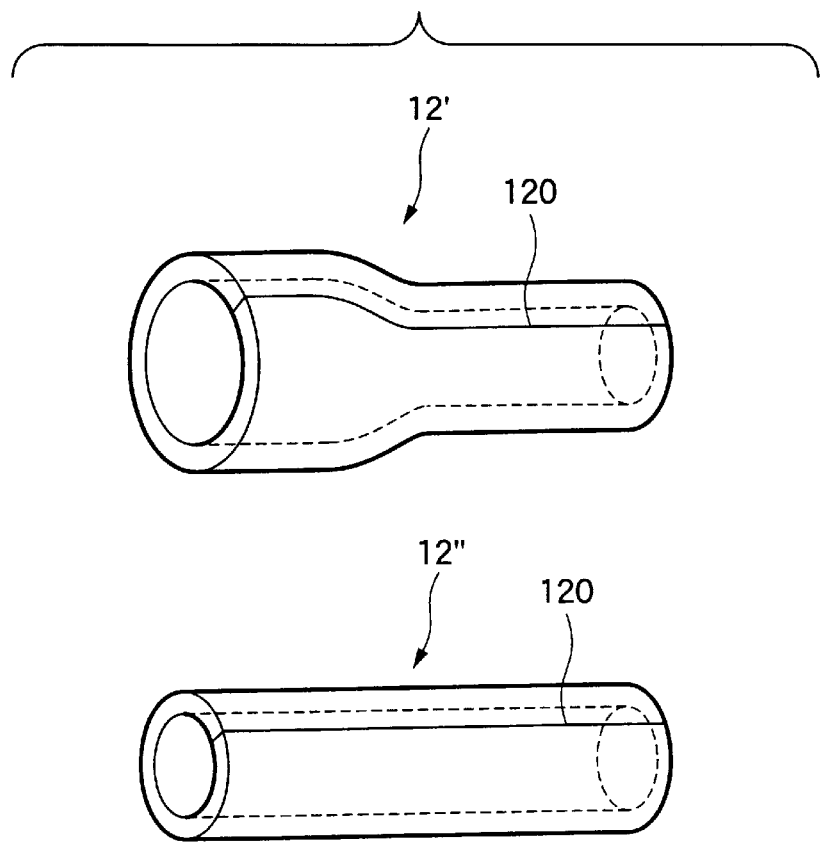
Fig. 10 is a perspective view of a tubular workpiece according to a second embodiment of the invention.
Figure 11:
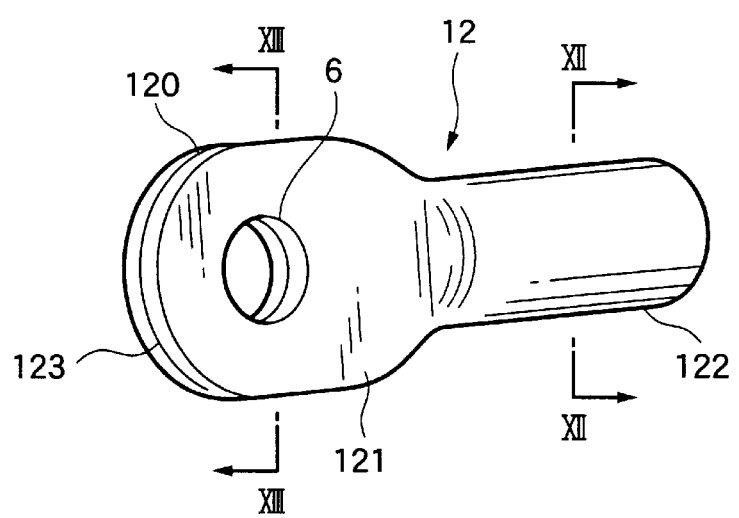
FIG. 11 is a perspective view of a wire connecting link according to the second embodiment of the invention.
Figure 12:
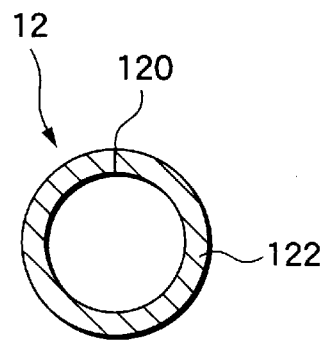
FIG. 12 is section XII—XII of FIG. 11.
Figure 13:
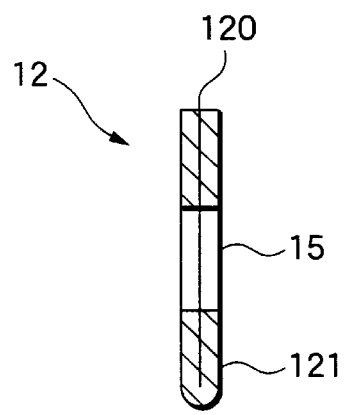
FIG. 13 is section XIII—XIII of FIG. 11.

FIG. 11 shows the wire connecting link 12 fabricated from one of the tubings shown in FIG. 10. FIGS. 12 and 13 are sections XII—XII and XIII—XIII, respectively, of FIG. 11. During a brazing operation, air finds an efficient way out through the open seam 120; however, since the seam 120 is eventually closed by brazing, the wire connecting link 12 has no problems with strength.

The concept of the invention may be applied to various endoscopic treatment instruments other than forceps.

Figure 15:
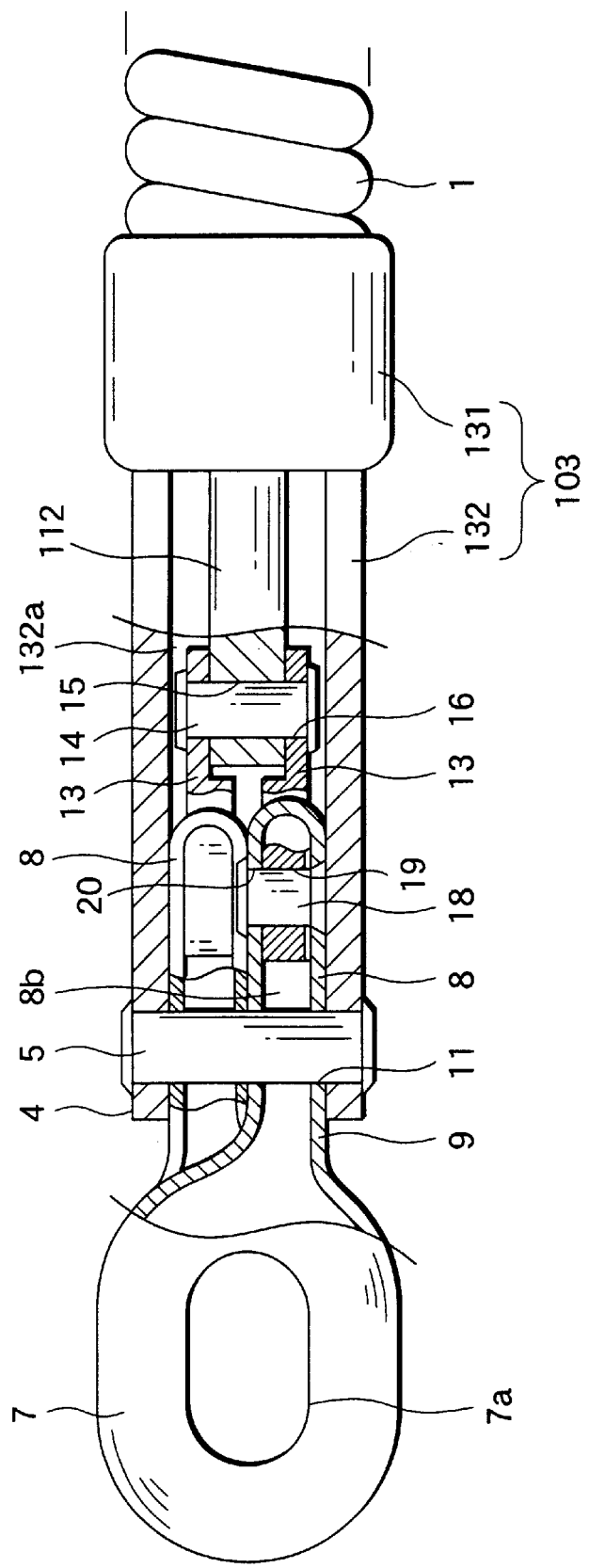
FIG. 15 is a plan view showing different sections of the distal end portion of endoscopic biopsy forceps in a closed state according to a third embodiment of the invention.
Figure 16:
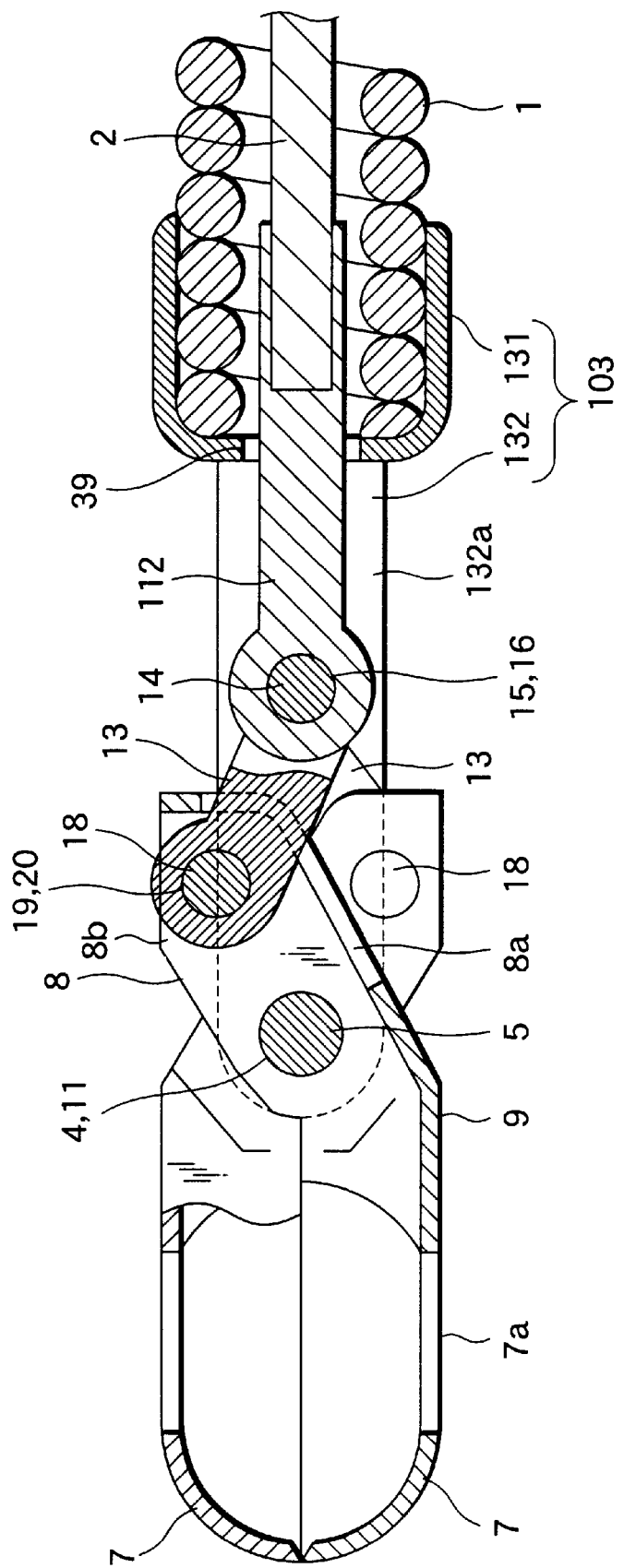
FIG. 16 is a side view showing different sections of the distal end portion of the same endoscopic biopsy forceps in a closed state.
Figure 17:
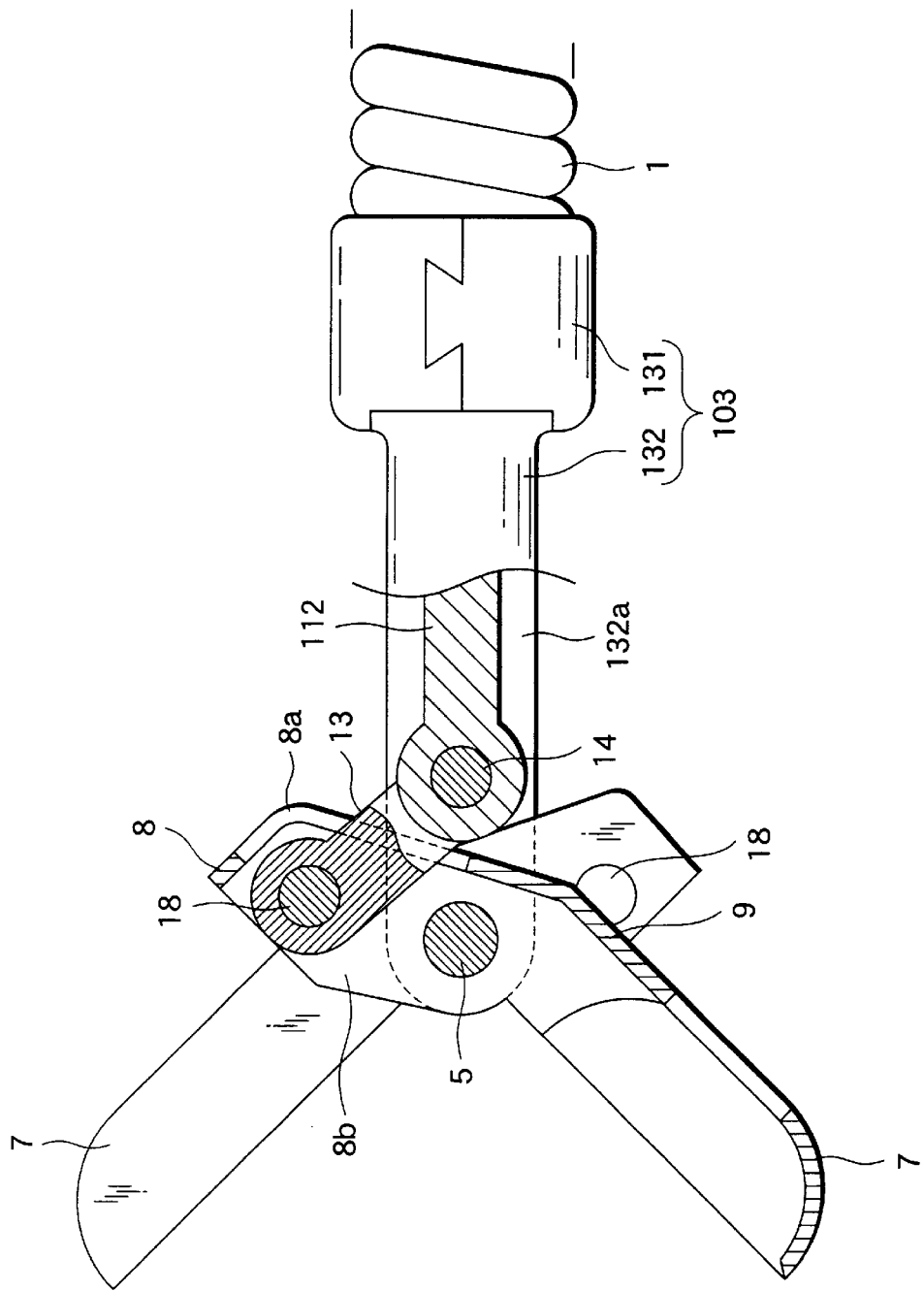
FIG. 17 is a side view showing, with part in section, the distal end portion of the same endoscopic biopsy forceps in an open state.

FIGS. 15, 16 and 17 show the distal end portion of an endoscopic biopsy forceps according to a third embodiment of the present invention.

Figure 18:
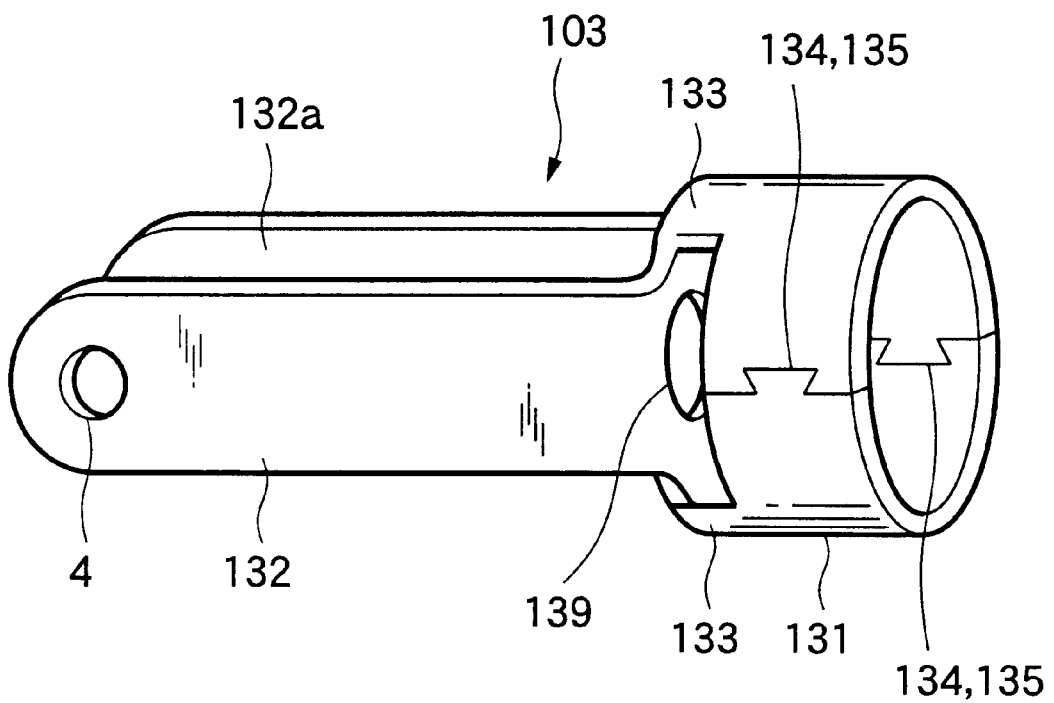
FIG. 18 is a perspective view showing a distal end support member of the same endoscopic biopsy forceps.
Figure 19:
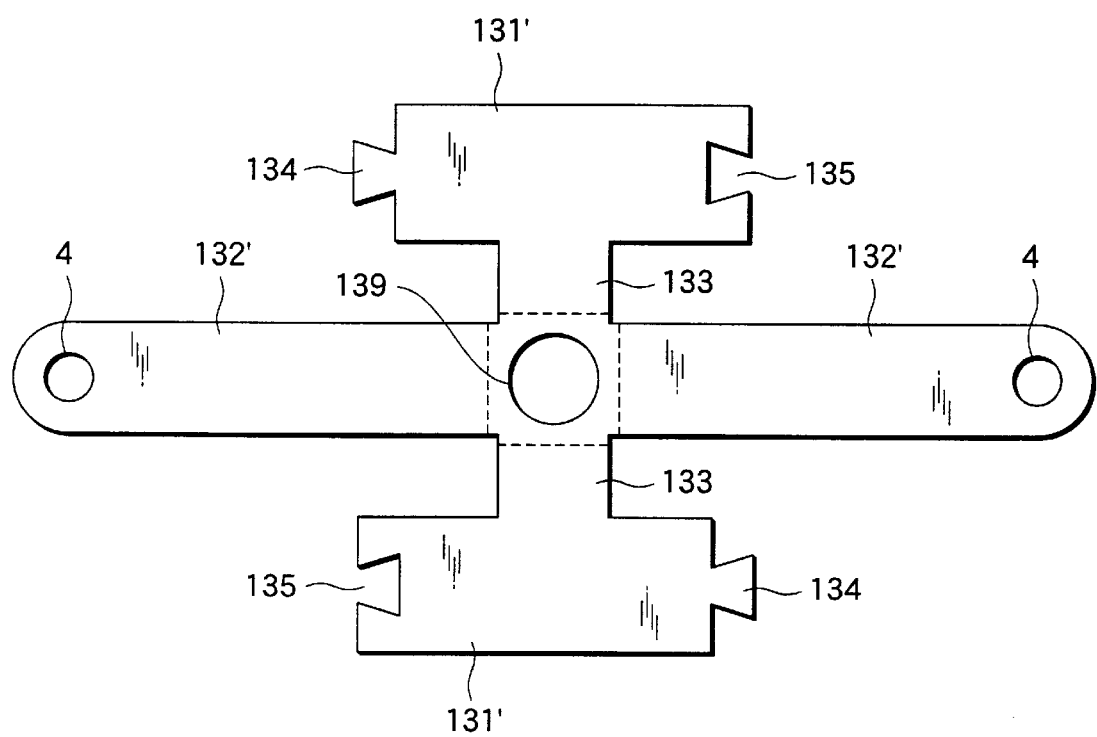
FIG. 19 shows the distal end support member in an unfolded state.

A distal end support member 103 used in the endoscopic biopsy forceps shown in FIGS. 15, 16 and 17 is shown in FIG. 18 and in an unfolded state in FIG. 19. The distal end support member 103 includes a sheath connector 131 formed in an annular shape that is connectable to the distal end of the sheath 1, and a drive mechanism holding groove 132 formed in a U-shape such that a distal end treatment member drive mechanism (e.g. drive levers 8 and link plates 13) can be held in a movable fashion. The sheath connector 131 and the drive mechanism holding groove 132 are formed by bending a single flat metal sheet. Details of the distal end support member 103 are given below.

Figure 14:
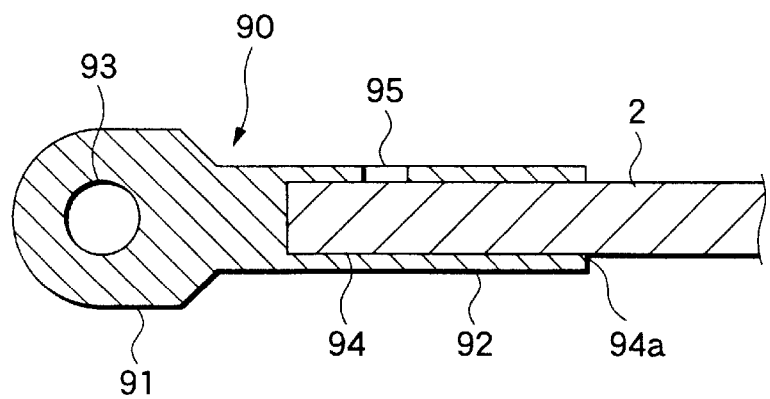
FIG. 14 is a side view showing in section a manipulating wire as connected to a wire connecting link used in an endoscopic biopsy forceps shown in FIG. 20.
Figure 32:
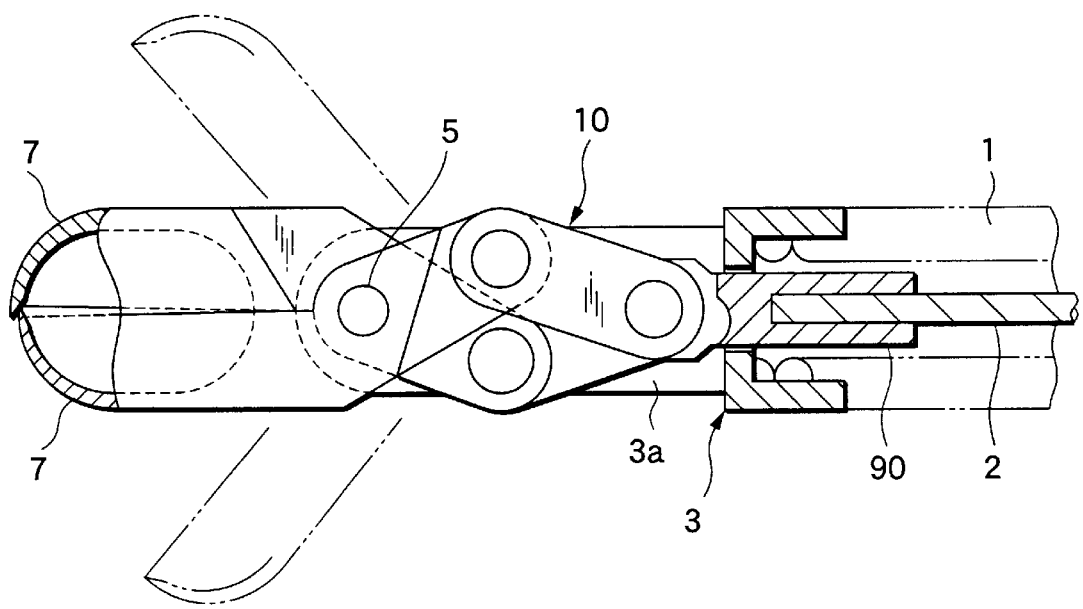
FIG. 32 is a side view showing, in partial section, the distal end portion of the endoscopic biopsy forceps that employs the wire connecting link shown in FIG. 14.
Figure 33:
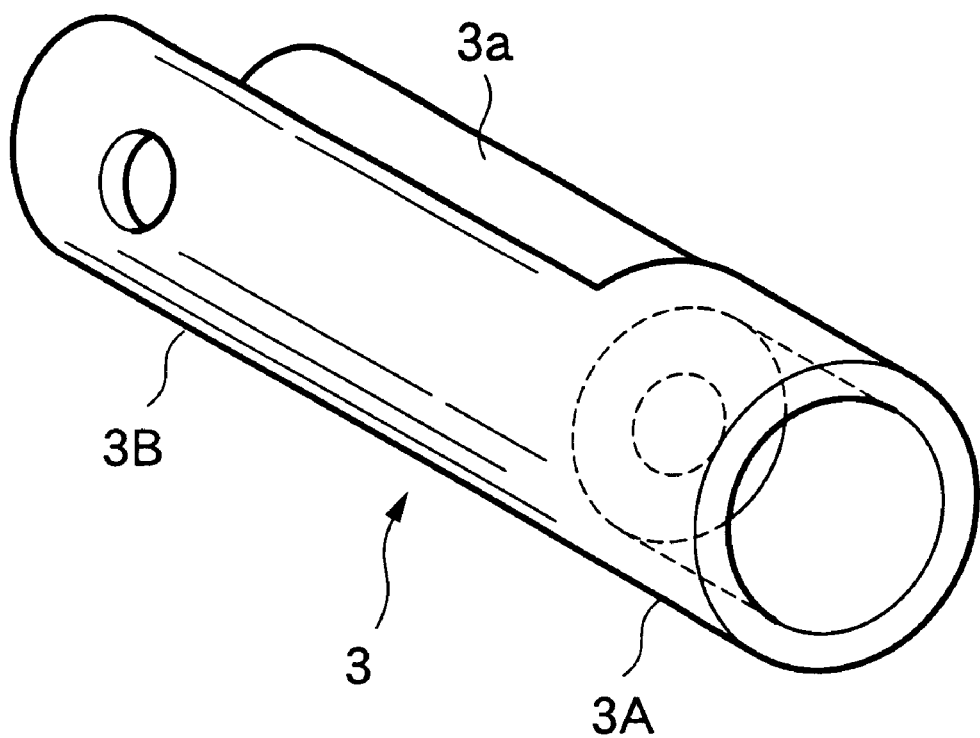
FIG. 33 is a perspective view of a distal end support member used in the endoscopic biopsy forceps shown in FIG. 32.

The boundary between the sheath connector 131 and the drive mechanism holding groove 132 has a hole 139 through which a wire connecting link 112 passes loosely along the central axis of the distal end support member 103. In this embodiment, the wire connecting link 112 similar in construction to the wire connecting link 90 shown in FIGS. 14 and 32 is used, but preferably replaced with the wire connecting link 12 described with reference to the first and second embodiments.

The link plates 13 are disposed within the parallel grooves 8b in the drive levers 8 and in engagement with rivets 18 each being received at opposite ends by the associated drive lever 8; hence, the link plates 13 and the drive levers 8 operate smoothly without skewing or leaning at the joints, allowing the forceps cups 7 to open and close in a positive manner. In a use mode, a mucosal tissue of a living body is held firmly between the two forceps cups 7 and torn off to be collected within the cups 7.

As shown in FIG. 19, a metal sheet from which the distal end support member 103 is to be fabricated has an elongated first strip 132' and a pair of second strips 131' connected to opposite sides of the first strip 132' via joints 133. The second strips 131' are parallel to the first strip 132', and each joint 133 is positioned at right angles to the middle of the first and second strips to make a single blank. Shown by 139 is the hole through which the wire connecting link 112 passes, and 4 is a support shaft receiving hole.

The drive mechanism holding groove 132 is formed by bending the first strip 132' in a U-shape. To form the sheath connector 131, the second strips 31' as well as the joints 133 are bent at right angles in a direction away from the first strip 132', and the second strips 131' alone are further curved in an annular shape.

The first strip 132' is formed to be thicker than the other parts of the blank, typically about twice as thick, to ensure mechanical strength. Such difference in thickness can typically be imparted by pressing. Note that instead of providing the two second strips 131' on opposite sides of the first strip 132', an elongated second strip may be provided on only one side of the first strip.

In the embodiment under consideration, the second strips 131' are each formed in a length just one half the circumference of the annular sheath connector 131, and the two second strips are curved in semicircles and joined in a continuous ring to form the sheath connector 131.

The joining parts of the second strips 131' have interlocking portions that are so shaped as to prevent said joining parts from slipping out of each other in a circumferential direction. In the embodiment under consideration, the interlocking portions are made up of male projections 134 in an inverted trapezoidal form and female cutouts 135 that are identical in shape to the male projections and in which they fit snugly.

Because of this design, the annular shape of the sheath connector 131 will not become distorted even if it is placed under a great force in a circumferential direction. If the male projections 134 are fitted in the female cutouts 135 and the joints are welded or otherwise fixed firmly, the sheath connector 131 will not be distorted in a radial direction, either.

Thus, the distal end support member 103 does not require any cutting operations on a milling machine or the like but it can be fabricated mostly by press working, contributing to a substantial reduction in the manufacturing cost.

Figure 20:
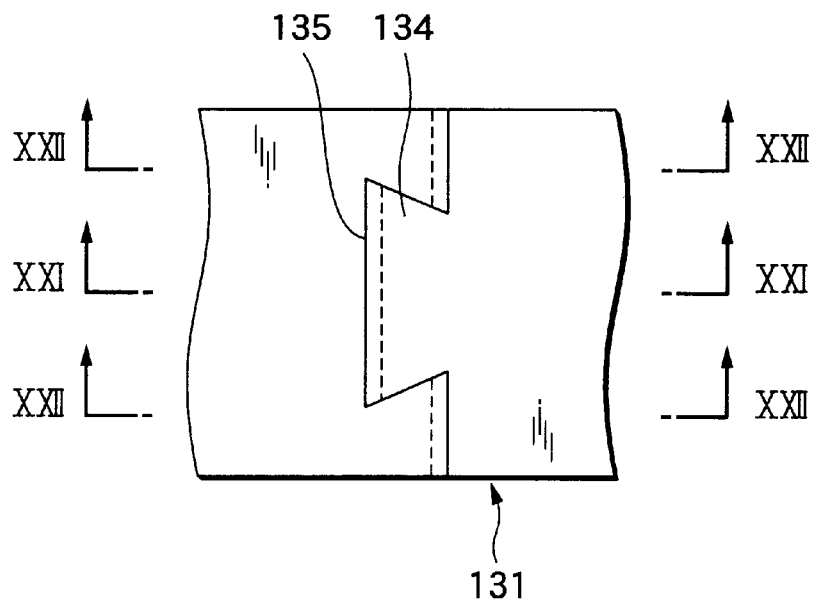
FIG. 20 is a front view of the joining parts of the distal end support member.
Figure 21:
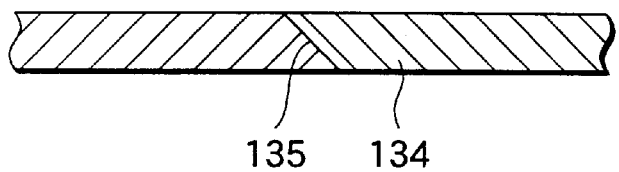
FIG. 21 is section XXI—XXI of FIG. 20.
Figure 22:
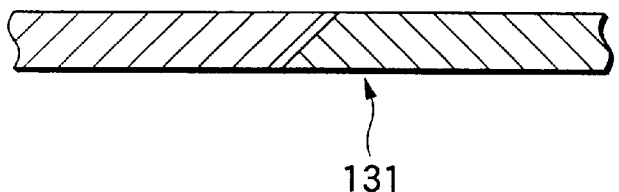
FIG. 22 is section XXII—XXII of FIG. 20.

As shown in FIG. 20, as well as in FIGS. 21 and 22 which are sections XXI—XXI and XXII—XXII, respectively, of FIG. 20, if the end faces of the joining parts of the sheath connector 131 are partly formed as a plurality of inclined surfaces that contact each other at an angle such that one joining part underlies the other joining part in a radial direction and that an area where one joining part underlies the other joining part alternates with an area where said one joining part overlies the other joining part, the overlying layer of one joining part presses down the underlying layer of the other joining part whereas the overlying layers of the other joining part press down the underlying layers of one joining part, preventing radial distortion of the sheath connector 131 in the absence of welding or other fixing of the male projections 134 and the female cutouts 135. While the inclined surfaces can be formed by pressing, they may also be formed by other working operations such as etching.

Figure 23:
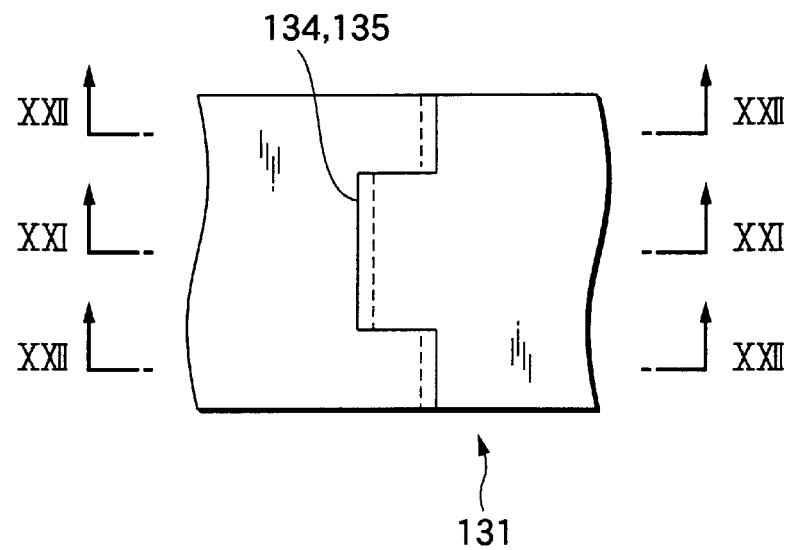
FIG. 23 is a front view of a first modification of the joining parts of the distal end support member.

The interlocking portions 134 and 135 may have a rectangular shape as shown in FIG. 23. If the end faces of these interlocking portions are inclined similarly to those shown in FIG. 20, they do not serve as anti-slip means but can prevent radial distortion of the sheath connector 31.

Figure 24:
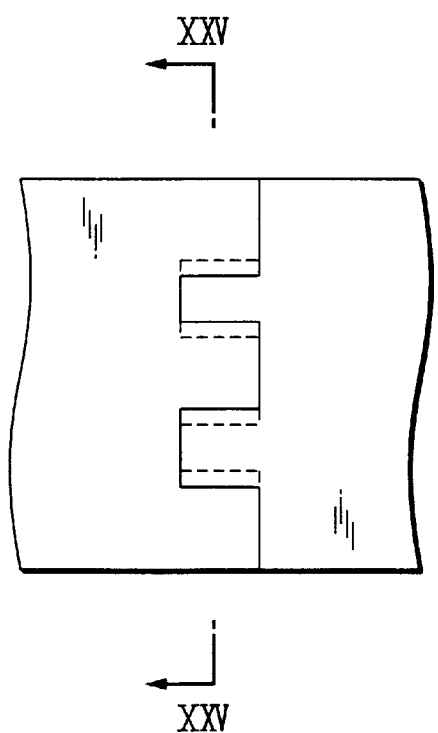
FIG. 24 is a front view of a second modification of the joining parts of the distal end support member.
Figure 27:
FIG. 27 is section XXVII—XXVII of FIG. 26.

Alternatively, as shown in FIG. 24 and FIG. 25 which is section XXV—XXV of FIG. 24, or in FIG. 26 and FIG. 27 which is section XXVII—XXVII of FIG. 26, interlocking rectangular male and female portions may be so shaped that their circumferential mating faces are inclined similarly to those shown in FIG. 20. Again, they do not serve as anti-slip means but can prevent radial distortion of the sheath connector 31.

Figure 28:
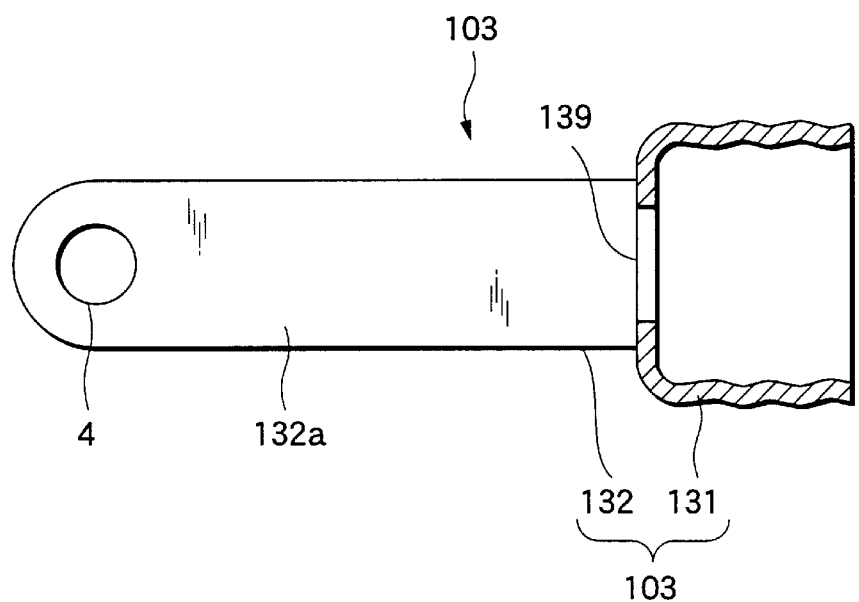
FIG. 28 is a side view showing, in partial section, a fourth modification of the joining parts of the distal end support member.
Figure 29:
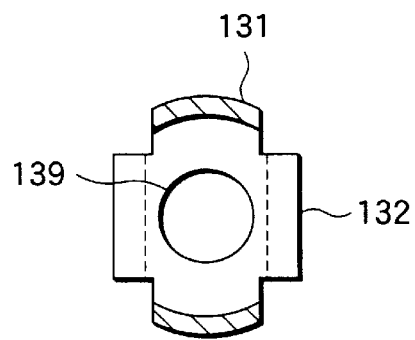
FIG. 29 is a front view showing, in partial section, a fifth modification of the joining parts of the distal end support member.
Figure 30:
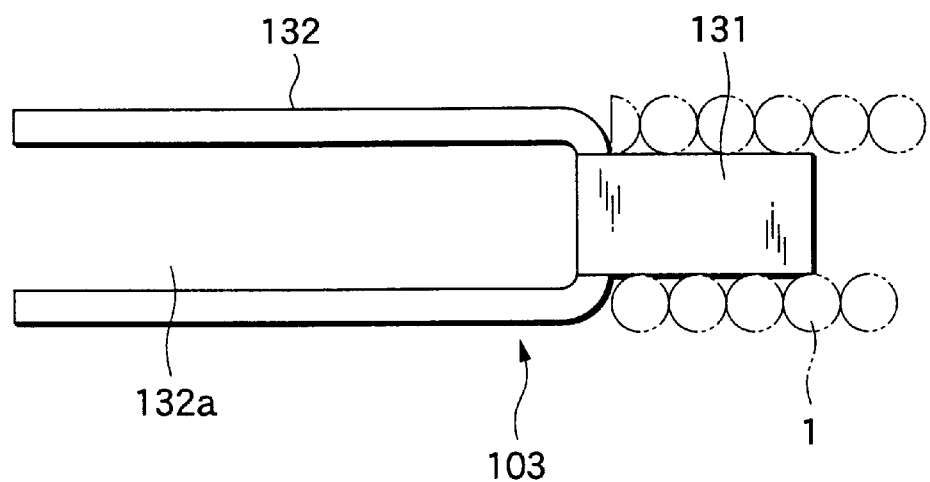
FIG. 30 is a plan view of a sixth modification of the joining parts of the distal end support member.
Figure 31:
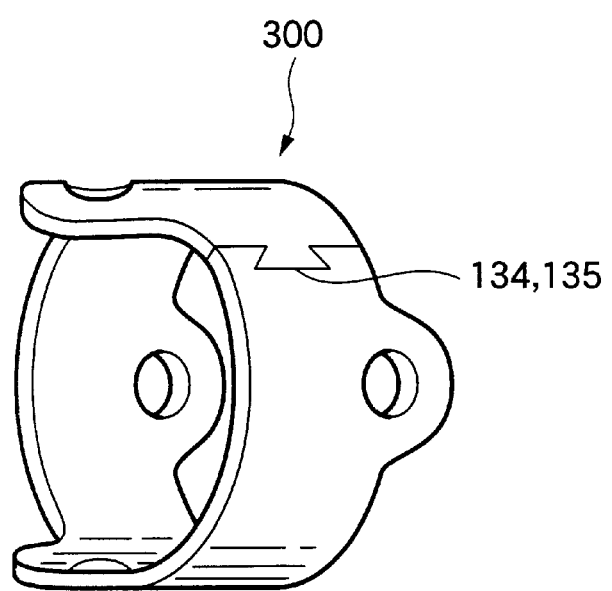
FIG. 31 a perspective view of the joint structure of the invention as applied to a joint ring in the curved portion of an endoscope.

In another embodiment of the invention, the sheath connector 131 may be formed as a cap with a spiral groove that can be threaded onto the sheath 1 as shown in FIG. 28. Alternatively, the sheath connector 131 may be formed of interrupted parts of a ring as shown in FIG. 29 (that is, the sheath connector 131 may be formed of plural portions spaced at given intervals in the circumferential direction). If desired, the sheath connector 131 may be so shaped that it can be inserted into the sheath 1 as shown in FIG. 30.

The concept of the invention may be applied to various endoscopic treatment instruments other than biopsy forceps. If desired, the joint structure of the invention may be applied to annular parts of an endoscope such as a joint ring 300 forming a curved portion of the endoscope.

What is claimed is:

1. A distal end support member adapted to movably hold a distal end treatment member drive mechanism on a distal end of a sheath of an endoscopic treatment instrument, said support member comprising:

a drive mechanism holding groove formed by bending a first strip of a metal blank in a U-shape; and a sheath connector formed by bending a second strip at right angles in a direction away from the first strip and then into an annular shape.

2. The support member according to claim 1, wherein the second strip is formed by two parts connecting to opposite sides of the first strip.

3. The support member according to claim 1, wherein the first strip is thicker than the other parts of the blank.

4. The support member according to claim 1, wherein the sheath connector formed as a single ring having joining parts.

5. The support member according to claim 4, wherein the joining parts of the sheath connector have interlocking portions that prevent the joining parts from slipping out of each other in a circumferential direction.

6. The support member according to claim 4, wherein end faces of the joining parts of the sheath connector include a plurality of inclined surfaces that contact each other at an angle such that one joining part underlies the other joining part in a radial direction and that an area where one joining part underlies the other joining part alternates with an area where said one joining part overlies the other joining part.

* * * * *